(12) United States Patent
Latterman

(10) Patent No.: US 10,149,637 B2
(45) Date of Patent: Dec. 11, 2018

(54) METHODS AND SYSTEMS FOR SIZING AN ORTHOTIC DEVICE

(71) Applicant: Sue Ann Latterman, Mill Valley, CA (US)

(72) Inventor: Sue Ann Latterman, Mill Valley, CA (US)

(*) Notice: Subject to any disclaimer, the term of this patent is extended or adjusted under 35 U.S.C. 154(b) by 204 days.

(21) Appl. No.: 15/204,637

(22) Filed: Jul. 7, 2016

(65) Prior Publication Data

US 2017/0007160 A1    Jan. 12, 2017

Related U.S. Application Data

(60) Provisional application No. 62/189,620, filed on Jul. 7, 2015.

(51) Int. Cl.
| | | |
|---|---|---|
| *A61B 5/107* | (2006.01) | |
| *A43B 7/14* | (2006.01) | |
| *A43B 7/28* | (2006.01) | |
| *A43D 1/02* | (2006.01) | |

(52) U.S. Cl.
CPC .......... *A61B 5/1074* (2013.01); *A43B 7/142* (2013.01); *A43B 7/28* (2013.01); *A43D 1/02* (2013.01); *A61B 5/1072* (2013.01)

(58) Field of Classification Search
CPC ..................................................... A61B 5/1074
USPC ........................................ 33/512, 6; 600/592
See application file for complete search history.

(56) References Cited

U.S. PATENT DOCUMENTS

| | | | | |
|---|---|---|---|---|
| 1,725,334 | A | | 8/1929 | Brannock |
| 4,917,105 | A | * | 4/1990 | Tiitola ................. A61B 5/1074 33/515 |
| 5,025,476 | A | * | 6/1991 | Gould .................. A61B 5/1074 33/3 B |
| 5,842,294 | A | | 12/1998 | Fabricant |
| 6,205,230 | B1 | * | 3/2001 | Sundman ............. A61B 5/0064 382/100 |
| 6,604,301 | B1 | * | 8/2003 | Manoli, II ............. A43B 7/141 36/144 |
| 7,367,074 | B1 | | 5/2008 | Bergquist |
| 7,926,363 | B2 | | 4/2011 | Miller et al. |
| 8,036,768 | B2 | | 10/2011 | Lowe |

(Continued)

OTHER PUBLICATIONS

International Search Report from International Application No. PCT/US2016/041362 dated Dec. 13, 2016.

(Continued)

*Primary Examiner* — Christopher W Fulton
(74) *Attorney, Agent, or Firm* — McDermott Will & Emery LLP

(57) ABSTRACT

A method for selecting size of an orthotic for a foot is described, where the method comprises collecting certain measurements for a foot, such as a length $l_1$ corresponding to a distance from a proximal point of the heel to a base of a metatarsal head and, optionally, a width w corresponding to a distance from the medial edge of the foot at approximately the base of the first metatarsal head to the lateral edge of the foot at approximately the base of the fifth metatarsal head, and, optionally, a height h corresponding to the height of the lateral foot arch relative to ground. The height h is measured, in some cases, with the foot in an adjusted or restored condition. The measurements are used to recommend or to select a size of an orthotic product.

14 Claims, 14 Drawing Sheets

(56) References Cited

U.S. PATENT DOCUMENTS

| | | | |
|---|---|---|---|
| 8,075,501 B2 | 12/2011 | Miller et al. | |
| 8,109,014 B2 | 2/2012 | Miller et al. | |
| 8,290,739 B2* | 10/2012 | Tadin | A61B 5/1036 33/512 |
| 8,596,145 B2 | 12/2013 | Miller et al. | |
| 9,778,027 B1* | 10/2017 | Smith | G01B 11/24 |
| 2004/0181976 A1 | 9/2004 | Copesky et al. | |
| 2005/0061332 A1* | 3/2005 | Greenawalt | A43D 1/025 128/882 |
| 2006/0283243 A1* | 12/2006 | Peterson | A61B 5/1036 73/172 |
| 2007/0043582 A1* | 2/2007 | Peveto | A43B 3/26 705/1.1 |
| 2008/0083416 A1* | 4/2008 | Xia | A43B 7/142 132/200 |
| 2008/0167582 A1 | 7/2008 | Shavelson | |
| 2009/0071038 A1 | 3/2009 | Luthi et al. | |
| 2009/0076772 A1 | 3/2009 | Hinshaw et al. | |
| 2012/0085001 A1 | 4/2012 | Miller et al. | |
| 2012/0143092 A1 | 6/2012 | Xia et al. | |
| 2014/0309534 A1 | 10/2014 | Pichler et al. | |
| 2014/0360033 A1 | 12/2014 | Miller et al. | |
| 2016/0110479 A1* | 4/2016 | Li | G06F 3/0484 703/1 |
| 2016/0249829 A1* | 9/2016 | Trabia | A61B 5/6892 600/592 |

OTHER PUBLICATIONS

Michaud, "An easy in-office test to evaluate foot function", Dynamic Chiropractic, The Chiropractic News Source, An MPA Media Publication, vol. 33, Issue 3, (2015), Online article retrieved from the internet: http://www.dynamicchiropractic.com/pdf_out/DynamicChiropractic.com-An-Easy-In-Office-Test-to-Evaluate-Foot-Function-1483743660.pdf.

Tedroff et al., "What has feet to do with it? Pes planus and Medial arch height in adults with and without autism spectrum disorder", Research in autism spectrum disorders, vol. 7, Issue 1, pp. 187-192 (2013) Particularly "Foot arch height" Section 2.2.2, pp. 189-190, and Figure 3, "Measuring the medial foot arch height with a verniper Caliper" pp. 190.

Powerstep, "Signature series leather ¾ length" Brochure, Stable Step LLC, 1 page (2013) retrieved from the internet: https://www.powersteps.com/images/pdf/spec_signatureleather34.pdf.

\* cited by examiner

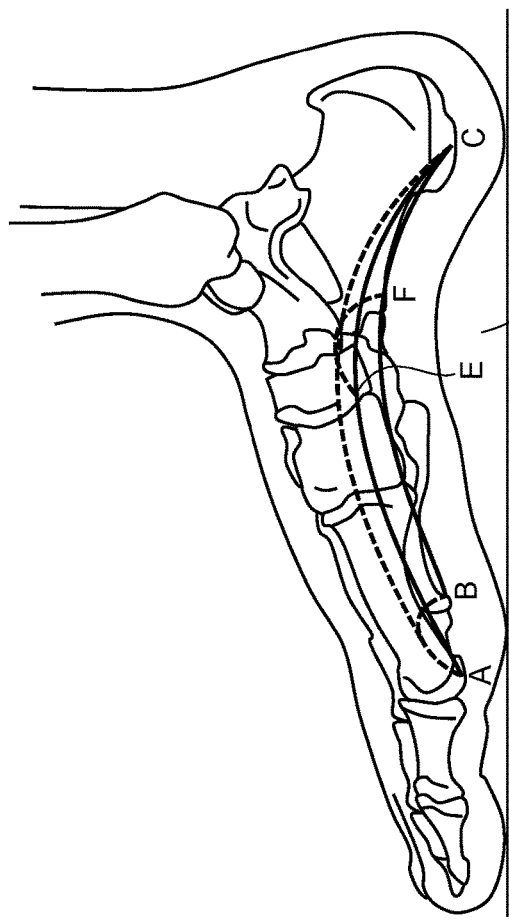
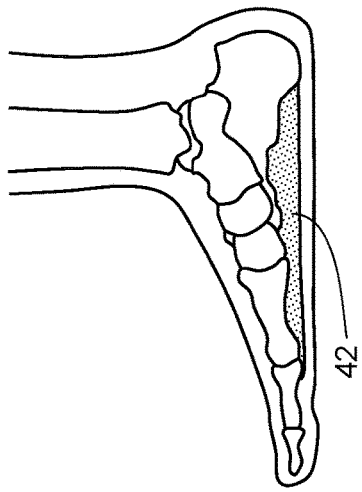
FIG. 2B
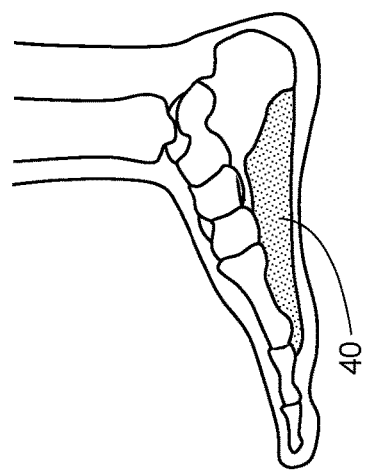
FIG. 2D
FIG. 2C
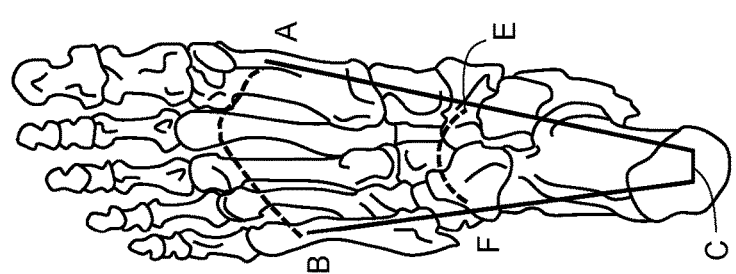
FIG. 2A

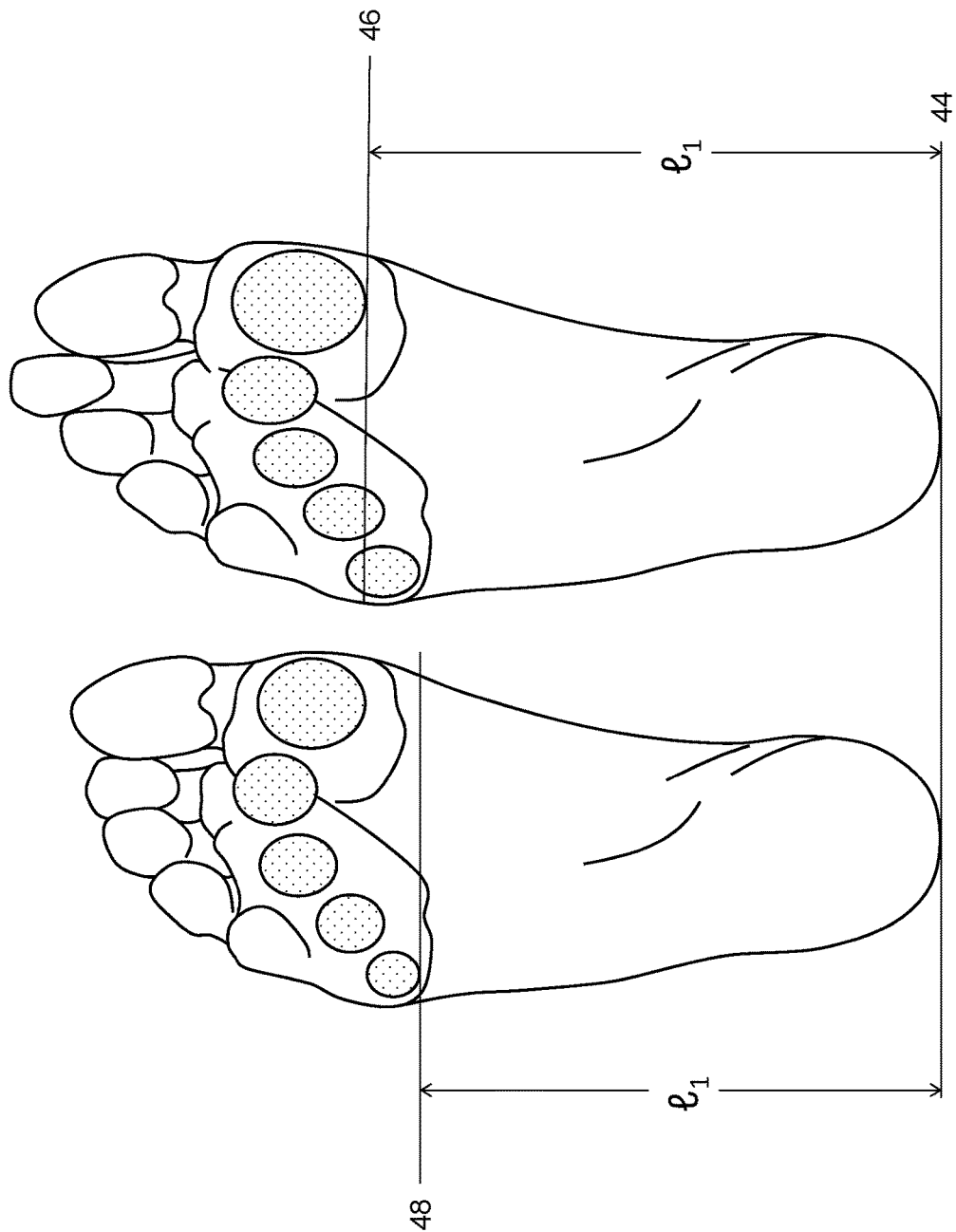

Plantar view of right foot

A = just proximal to base of 1st metatarsal head
B = just proximal to base of 5th metatarsal head
C = center bottom of heel where it touches ground
D = Peak of area created by restored 3 arches Lateral view of right foot Plantar Vault $h$ = Lateral Arch Height

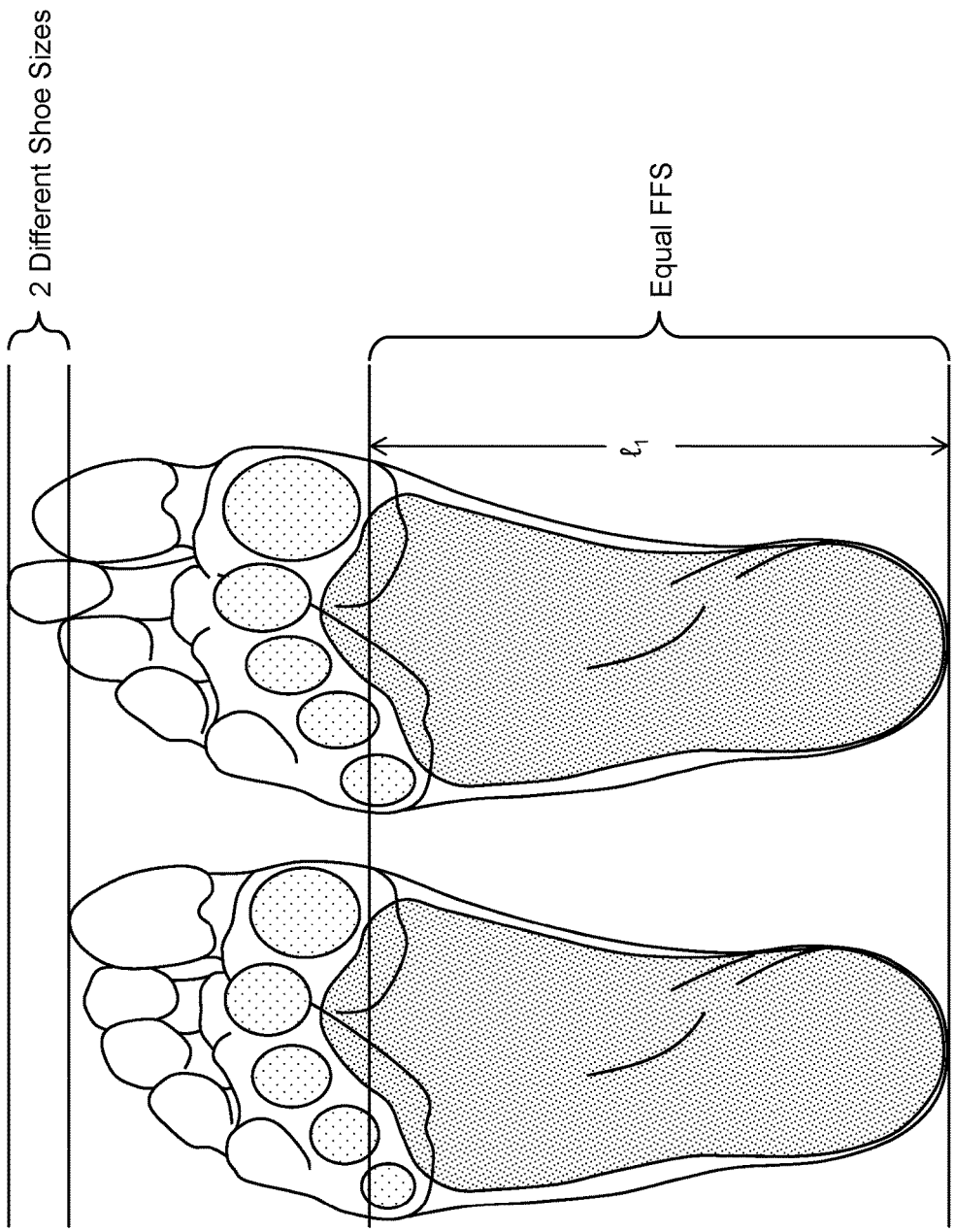

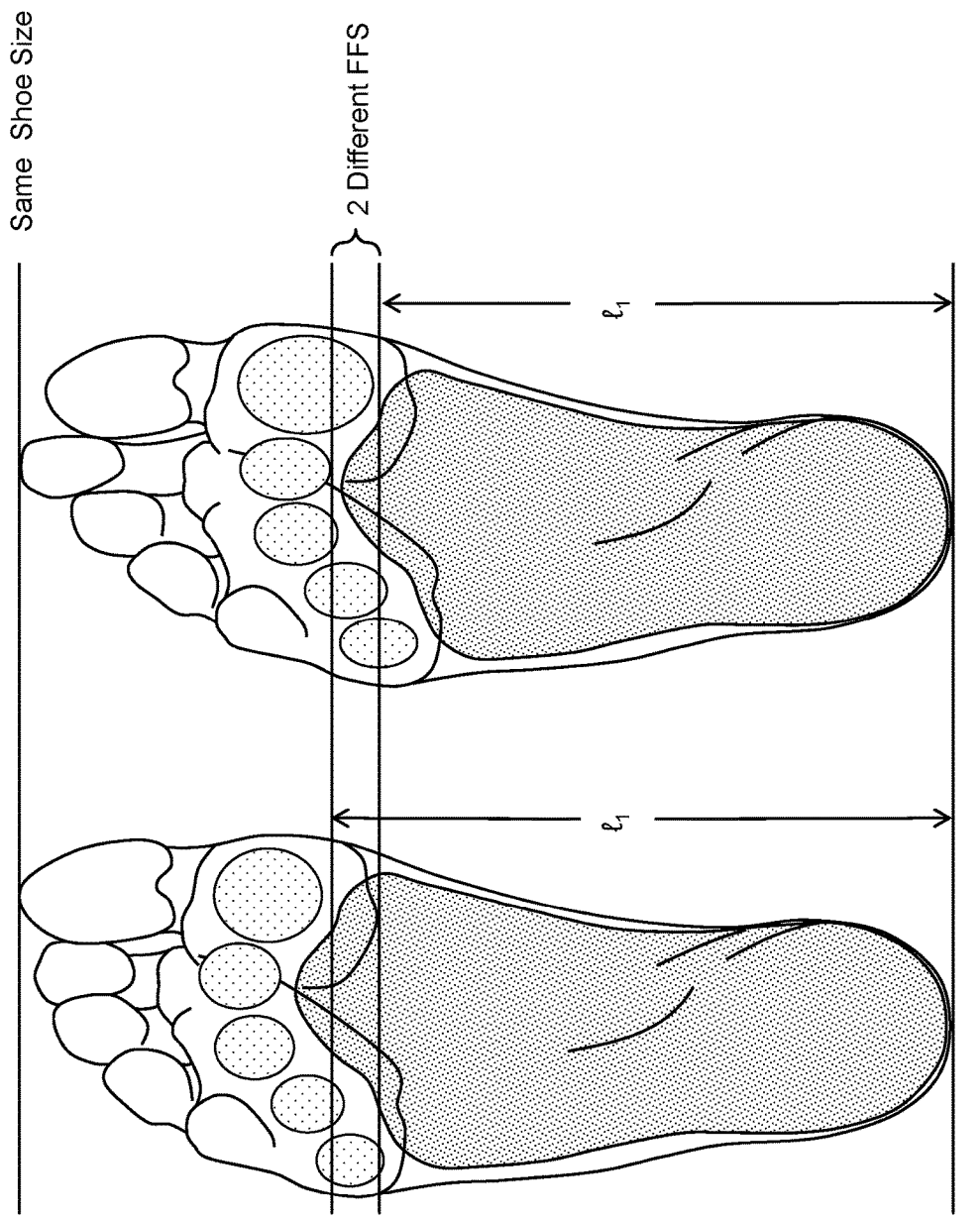

METHODS AND SYSTEMS FOR SIZING AN ORTHOTIC DEVICE

CROSS-REFERENCE TO RELATED APPLICATIONS

This application claims the benefit of U.S. Provisional Application No. 62/189,620, filed Jul. 7, 2015, which is incorporated by reference herein.

TECHNICAL FIELD

The subject matter described herein relates to a method for sizing an orthotic device for a foot, a scheme for sizing orthotic devices and a method for determining a correctly sized foot orthotic.

BACKGROUND

It has been historically believed that the human foot differs substantially when comparing the feet of individuals, and that a single individual can have significant differences between their right and left feet. These differences have to date resulted in a number of possibilities when trying to classify and categorize human feet into groups in order to aid in the diagnosis and treatment of various pedal and postural conditions and diseases. Early prior art methods for classifying foot types grouped feet according to specific characteristics, such as the type of medical arch—low, normal and high, and supinated or pronated. Feet have also been typed according to toe curvature and shape into, for example, a "Greek Foot" or a "Roman Foot." These simple classification systems continue to be used by practitioners to diagnose and treat conditions, as well as to facilitate the fabrication of shoe lasts, insoles and orthotics.

Orthotics are shoe inserts or shoe soles/beds intended to improve foot function and minimize stress forces that may cause foot deformity and pain. It is becoming increasingly common for individuals to have sport-specific footwear custom made for multidirectional sports or edge-control sports by casting the foot within the footwear, such as a ski boot, ice skate boot, biking shoes, or inline skate boot. A large variety of "comfort" shoes are also being designed in an attempt to help the growing number of people now suffering from foot, leg and back pain. Orthotics, whether insertable into footwear or integral with customized footwear, have been designed and selected to make standing, walking, running and other physical activities more comfortable and efficient by altering the angles at which the foot strikes a surface. Sometimes these orthotics and specialized shoes simply splint (immobilize) the foot's joints as a means to decrease foot pain. These common approaches, however, do not restore alignment of the foot structures (bones, joints, ligaments, etc.) to the physiologic natural condition, and therefore do not optimize foot function. The common approaches to select a so-called "customized" orthotic—including taking a mold of the subject's foot (feet), measuring the length of the individual's foot from heel to tip of the toes, sometimes in combination with a medial arch height measurement or, more recently, measuring length of the foot (from heel to tip of toes) in combination with pressure measurements while standing or transposing two dimensional photographs of a foot into a three dimensional orthotic, fail to place the foot structures in a state that optimally restores alignment of the foot structures and properly distributes pressure across the foot surface.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method for selecting size of a foot orthotic is provided. The method comprises determining a length $l_1$ corresponding to a distance from a back of a heel to approximately a base of a metatarsal head of a foot; and determining a height h of a lateral arch of the foot, the height h corresponding to a distance between a surface on which the foot is placed to a plantar surface of the foot approximately at an intersection defined by a lateral cuneiform bone, a navicular bone and a cuboid bone; and selecting a foot orthotic size based on length $l_1$ and height h.

In one embodiment, the length $l_1$ is taken as the distance from the back of the heel to the base of the first metatarsal head. In another embodiment, the length $l_1$ is taken as the distance from the back of the heel to the base of the fifth metatarsal head. In yet another embodiment, the length $l_1$ is taken from a most proximal point of the base of the heel.

In still another embodiment, determining a height h comprises determining the height h corresponding to a distance between a surface on which the foot is placed to a plantar surface of the foot in an area lateral to the intersection of the lateral cuneiform, navicular and cuboid bones.

In another embodiment, determining a length $l_1$, determining a height h or both is performed on a foot manipulated to adjust one or more bones of the foot to a restored position. In another embodiment, determining is performed on a foot that is manually manipulated to adjust one or more bones of the foot to a restored position. In yet another embodiment, determining is performed on a foot that is manipulated using a device or instrument to adjust one or more bones of the foot to a restored position. In one embodiment, the one or more bones comprise one or more bones in the midfoot, such as the lateral cuneiform-navicular-cuboid (LCNC) complex.

In another embodiment, the method further comprises determining a width w corresponding to a distance from a medial edge of the foot at approximately the base of the first metatarsal head to a lateral edge of the foot at approximately the base of the fifth metatarsal head.

In another embodiment, selecting a foot orthotic size comprises selecting a foot orthotic size based on length $l_1$ and height h and a foot orthotic width based on width w.

In some embodiments, reference to orthotic size intends size based on length $l_1$ only. In other embodiment, reference to orthotic size intends size based on length $l_1$ and height h. In other embodiments, reference to orthotic size intends size based on length $l_1$ and height h and width w. In some embodiment, orthotic size intends size based on length $l_1$ and/or height h and orthotic width intends a width that is based on width w.

In one embodiment, selecting a foot orthotic size comprises selecting a foot orthotic size based on length $l_1$ and a foot orthotic width based on width w.

In another embodiment, selecting further comprises selecting a foot orthotic size from a library of sizes (inclusive or exclusive of various widths) for foot orthotics.

In still another embodiment, selecting further comprises selecting a foot orthotic size from a library of sizes for foot orthotics is based on length $l_1$ and height h. In yet another embodiment, the library comprises a library of orthotic sizes based on length $l_1$ and height h, wherein each size is available in the library at more than one width.

In one embodiment, selecting from a library comprises selecting from a library of sizes for foot orthotics where determined height h correlates to a vacuity defined by medial, lateral and transverse foot arches relative to ground.

In some embodiments, the method additionally comprises correlating height h to a volume v from an array of values for volume v calculated based on a statistical relationship between height h and a vacuity defined by medial, lateral and transverse foot arches relative to ground. In another embodiment, height h is correlated to volume of a vacuity having a medial arch height, where the measured (lateral arch) height h is less than the medial arch height by a numerical factor. In one embodiment, the numerical factor is a value between about 0.45 cm and about 0.64 cm (0.18-0.25 inches) or between about 0.38 cm and about 0.76 cm (0.15-0.30 inches).

In another embodiment, the method comprises measuring (lateral arch) height h after manipulation of the foot to a restored state, calculating a medial arch height by decreasing the measured (lateral arch) height h by a numerical factor having a value between about 0.45 cm and about 0.64 cm (0.18-0.25 inches), and designing a custom orthotic based on the measured (lateral arch) height h and calculated medial arch height.

In one embodiment, the length $l_1$, the height h, or both are determined on a foot covered with a sock. In other embodiments, the length $l_1$, the height h, or both are determined on a naked foot. In other embodiments, the length $l_1$, the width w, or both are determined based on an image of a foot. In some embodiments, the image is selected from a cast or crush box impression, an x-ray image, a pressure map image, a photograph, a movie or a map constructed from a laser used to image the foot.

In another aspect, a method for selecting a size of a foot orthotic is provided. The method comprises determining at least two of the following measurements for a foot having a heel, a midfoot, a medial edge and a lateral foot arch: (i) a length $l_1$ corresponding to a distance from a proximal point of the heel to a base of a metatarsal head; (ii) a width w corresponding to a distance from the medial edge of the foot at approximately a base of a first metatarsal head to the lateral edge of the foot at approximately a base of a fifth metatarsal head; and (iii) a height h corresponding to a height of the lateral foot arch relative to ground. Based on the determined measurements, a size of a foot orthotic is recommended.

In one embodiment, length $l_1$ is taken as the distance from the proximal point of the heel to a base of a first metatarsal head. In another embodiment, length $l_1$ is taken as the distance from the proximal point of the heel to a base of a fifth metatarsal head.

In some embodiments, height h is measured after manual or automated manipulation of the foot to adjust one or more bones in the midfoot to a restored state.

In another embodiment, recommending comprises recommending a size from a library of foot orthotics that comprises orthotics with a size that correlates to length $l_1$. In another embodiment, recommending comprises recommending a size from a library of foot orthotics that comprises orthotics at one or more widths that accommodate measured width w. In still other embodiments, recommending a size comprises recommending a size that is based on length $l_1$ and width w. In yet other embodiments, recommending a size comprises recommending a size that is based on length $l_1$ or on height h. In another embodiment, recommending a size comprises recommending a size that is based on length $l_1$ or on height h and additionally recommending a width of an orthotic based on width w.

In some embodiments, recommending a size comprises recommending a size based on height h, where height h is correlated to a vacuity defined by medial, lateral and transverse foot arches relative to ground. In other embodiments, recommending a size comprises recommending a size based on height h, where height h is correlated to a volume v corresponding to a vacuity defined by the plantar topography of the foot and the ground while standing or while seated. In one embodiment, the vacuity has a volume v determined from a statistical average of measurements of the vacuity of feet in a population of feet after manipulation of each foot (manually or with an instrument) to position one or more bones in the midfoot to a restored state. The dimensions to determine volume of the vacuity are measured after manipulation of a foot, and the volume of vacuity is an average or median volume in a population of feet after manipulation of each foot. In one embodiment, the dimensions to ascertain volume of the vacuity are one or more of medial, lateral and transverse foot arches relative to a ground or plane.

In one embodiment, the volume v is selected from at least two volumes $v_1$ and $v_2$, which can be assigned an identifier, such as "low" or "medium", where the at least two volumes $v_1$ and $v_2$ are determined from vacuity measurements of a population of feet manipulated into an adjusted or restored state. In one embodiment, the volume v is selected from 2, 3, 4 or 5 volumes assigned an identifier, such as $v_1$, $v_2$, $v_3$, $v_4$, and $v_5$, or F, L, M, MH, H, where the at least two identified volumes were determined from vacuity measurements of a population of feet manipulated into an adjusted or restored state. The volume v can, in any of these embodiments, have a height dimension that is greater than the measured lateral arch height h by a numerical factor and/or that is less than a measured medial arch height relative to ground while sitting or standing or partially standing. In one embodiment, the measured medial arch height is reduced to an adjusted medial arch height such that the adjusted medial arch height is greater than the measured lateral arch height h by the numerical factor. The numerical factor can be a value between about 0.40-0.60 cm (0.16-0.24 inches), about 0.42-0.58 cm (about 0.16-0.23 inches), about 0.45 cm-0.64 cm (about 0.18-0.25 inches) or about 0.45-0.55 cm (about 0.18-0.22 inches), or about 0.47-0.52 cm (about 0.18-0.20) or about 0.38-0.76 cm (about 0.15-0.30 inches).

In another aspect, a system to determine size of a foot orthotic is provided. The system comprises instructions to measure a length $l_1$ corresponding to a distance from a proximal heel point to a base of the first or the fifth metatarsal head; and a size selection matrix that correlates length $l_1$ to a foot orthotic size.

In one embodiment, the instructions further comprise instructions to measure a width w corresponding to a distance from a medial edge of the foot at approximately the base of the first metatarsal head to the lateral edge of the foot at approximately the base of the fifth metatarsal head, and the matrix comprises a choice of orthotic width for each orthotic size.

In another embodiment, the instructions further comprise instructions to measure a height h corresponding to the height of the lateral foot arch relative to a ground (or a plane), and the matrix comprises a choice of orthotic volume determined from the measured height h for each orthotic size.

In yet another aspect, a system to determine size of a foot orthotic comprises instructions to measure at least two of (i) a length $l_1$ corresponding to a distance from a proximal heel point to a base of the first or the fifth metatarsal head; (ii) a width w corresponding to a distance from the medial edge of the foot at approximately the base of the first metatarsal head to the lateral edge of the foot at approximately the base of the fifth metatarsal head; and (iii) a height h corresponding to the height of the lateral foot arch relative to a ground (or a plane); and a size selection matrix that correlates the at least two measurements to an orthotic size.

In one embodiment, the system further comprises a device to measure length $l_1$ and width w. In another embodiment, the system further comprises a device to determine height h.

In another aspect, a library of foot orthotics is provided. The library comprises a collection of foot orthotics, each orthotic in the collection assigned a size that corresponds to a measurement of length $l_1$ taken as a distance from a proximal heel point to a base of the first or the fifth metatarsal head; wherein each size is provided in at least two different widths w.

In one embodiment, each size of orthotic in the collection is provided in at least two different heights h corresponding to the height of the lateral foot arch relative to ground (or a plane).

In another embodiment, each size of orthotic in the collection is provided in at least two different volumes corresponding to a vacuity defined by medial, lateral and transverse foot arches relative to ground (or a plane) and selected based on a user's measurement of height h of lateral foot arch relative to ground (or a plane).

In still another embodiment, the at least two different widths w correspond to a distance from a first metatarsal head medial edge to a fifth metatarsal head lateral edge measured in a population of human feet.

In yet another embodiment, each orthotic in the collection has an undulating distal trim line.

In other embodiments, each orthotic in the collection of foot orthotics is manufactured from a carbon fiber composite material, a plastic material, a thermoplastic material or a polymeric material or polymeric blend or a cork material.

In another embodiment, each orthotic is intended to be inserted into footwear. In another embodiment, each orthotic in the collection is a piece of footwear.

In addition to the exemplary aspects and embodiments described above, further aspects and embodiments will become apparent by reference to the drawings and by study of the following descriptions.

Additional embodiments of the present methods and systems, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIGS. 2A-2B show a plantar view and a medial side view of a foot and illustrate three arches of the foot;

FIGS. 2C-2D are medial side views of a foot showing different arch types;

FIGS. 3A-3B are plantar views of a foot showing approaches to determining one of the dimensions for sizing an orthotic in accord with an embodiment of the method herein;

FIG. 7A is a scan of a plantar foot surface with shading (in place of color) showing the height of the foot's arches, and FIG. 7B shows a three-dimensional depiction of FIG. 7A identifying the lateral arch height h;

FIGS. 11A-11B are plantar views of two different feet with different shoe sizes fitted with an orthotic device sized according to the method described, where the two feet have the same functional foot size (FFS) and thus require the same size of foot orthotic;

FIG. 12A-12B are plantar views of two different feet having the same shoe size fitted with an orthotic device sized according to the method described, wherein the two feet have different functional foot size (FFS) and thus require different sizes of foot orthotic; FIG. 13A shows an orthotic device having an undulating distal trim line on the foot, and FIGS. 13B-13C show how the length and width of the foot were measured to size the orthotic device.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to an "orthotic" includes a single orthotic as well as two or more of the same or different orthotics.

II. Method and System for Orthotic Sizing

Figure 1B:
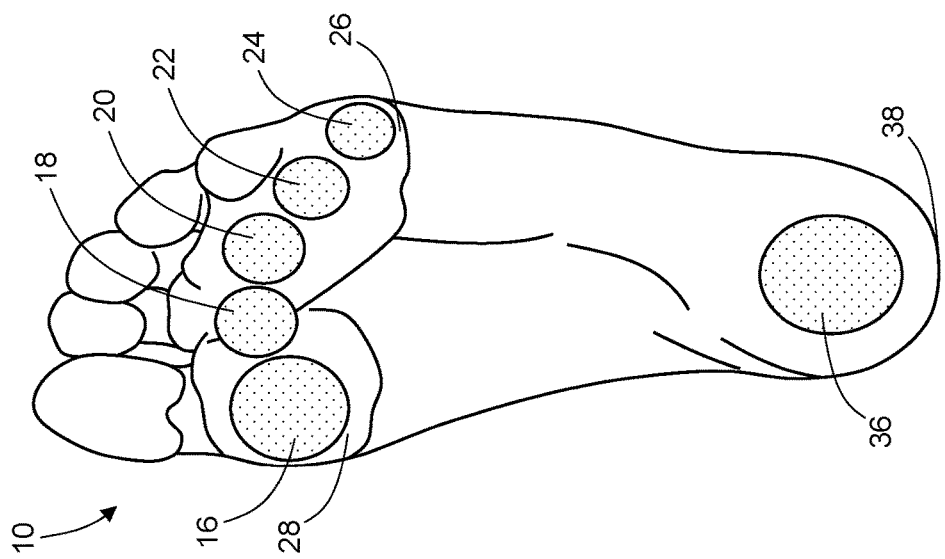
FIGS. 1A-1B are plantar views of a foot.
Figure 1A:
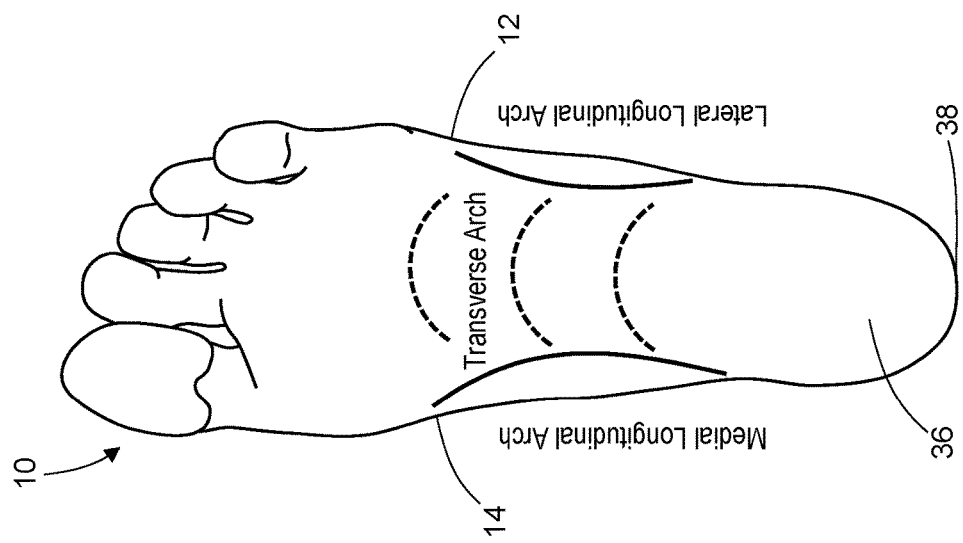
Figure 1C:
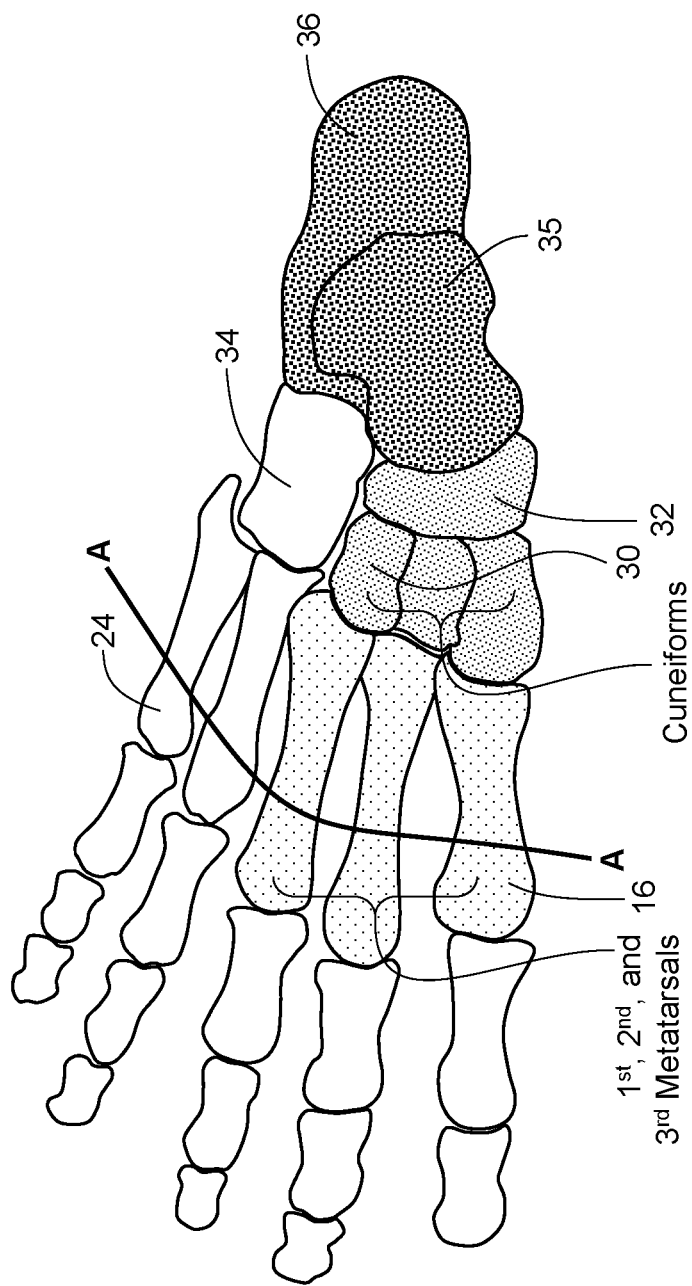
FIG. 1C is a top view of a foot skeleton.

In a first aspect, a method for selecting an orthotic size for a foot is provided. With reference to FIG. 1A, a plantar view of a foot 10 is shown. The lateral side of the foot is indicated as 12 and the medial side is indicated as 14. An illustration of foot 10 is shown in FIG. 1B where the approximate positions of the heads of the $1^{st}$, $2^{nd}$, $3^{rd}$, $4^{th}$ and $5^{th}$ metatarsal bones are indicated by identifiers 16, 18, 20, 22, and 24, respectively. The base of $5^{th}$ metatarsal head 24 is indicated at 26 and the base of $1^{st}$ metatarsal head 16 is indicated at 28. FIG. 1C shows the bones of the foot and further illustrates what is intended by approximately the "base of the first metatarsal head" and approximately the "base of the fifth metatarsal head." Each metatarsal bone is composed of a base, a body and a head. The base of a metatarsal bone is the part closest to the ankle and the head is closest to the toes. The narrowed part extending between the base and head is the body of the bone. The base of each metatarsal articulates with the cuboid bone (34) or with a cuneiform bone, where the three cuneiform bones are identified by the bracket identified as "cuneiforms." The head of each metatarsal at its distal point articulates with a phalange, and more specifically with a proximal phalanx of a phalange. The approximate base of the first metatarsal head and the approximate base of the fifth metatarsal head are indicated by the line designated as A-A in FIG. 1C, where line A-A shows the approximate base of all five metatarsal heads. FIG. 1C also illustrates the bones in what is referred to the "LCNC" complex—the lateral cuneiform, navicular and cuboid bones, identified as 30, 32 and 34, respectively. FIGS. 1A-1C also illustrate the talus bone (35) heel bone (calcaneus) 36, and with specific reference to FIGS. 1A-1B, the base or back 38 of the heel.

Arches of the foot are shown in FIGS. 2A-2B, where the lateral arch is indicated at line B-C and the medial arch at line A-C. Lines A-B and E-F designate the transverse metatarsal/tarsal arch. As a person of skill will appreciate, the height of the foot arches relate to what is commonly referred to as flat (or low) arches, normal (or medium) arches, or high arches. In a high arch foot, a footprint of the foot shows, at most, a thin line on the lateral side of the foot connecting the heel and the ball of the foot. The foot when in contact with the ground has a vacuity, also referred to in foot anatomy textbooks at the vault or dome, that corresponds to the empty space or gap between the ground and the plantar surface under the arch(es) that does not contact the ground. This is shown in FIGS. 2C-2D for a foot with a medium arch (FIG. 2C) and for a foot with a flattened or low arch (FIG. 2D), where the vacuity is denoted by the identifiers 40 and 42, respectively, and is also shown in a dotted pattern to assist viewing the vacuity.

Accordingly, and with reference to FIGS. 1A-2D, in one embodiment, a method for determining a size of an orthotic device for a foot comprises determining a length $l_1$ corresponding to a distance from a base of the heel to a base of a metatarsal head. In one embodiment, the length $l_1$ corresponds to a distance from the base of the heel to the base of the $1^{st}$ metatarsal head. This embodiment is illustrated in FIG. 3A, where length $l_1$ corresponds to a distance from the base of the heel 44 to the base of the $1^{st}$ metatarsal head 46. In another embodiment, the length $l_1$ corresponds to a distance from the base of the heel to the base of the $5^{th}$ metatarsal head. This embodiment is illustrated in FIG. 3B, where length $l_1$ corresponds to a distance from the base of the heel 44 to the base of the 5th metatarsal head 48.

Figure 4A:
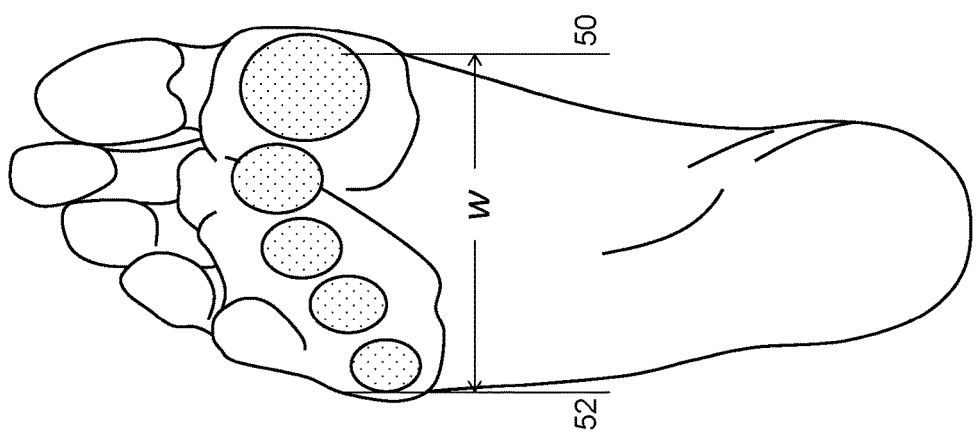
FIGS. 4A-4B are plantar views of a foot showing approaches to determining one of the dimensions for sizing an orthotic in accord with an embodiment of the method herein.
Figure 4B:
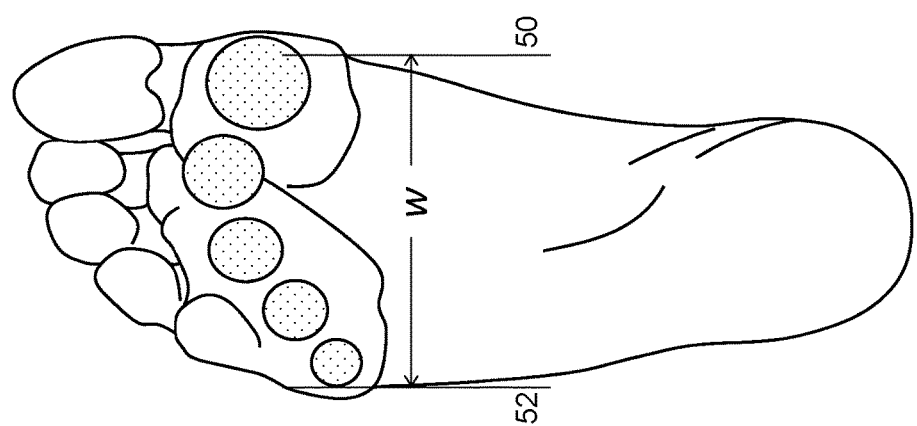

The method also comprises optionally measuring a width w corresponding to a distance from the medial edge of the foot at approximately the base of the $1^{st}$ metatarsal head to the lateral edge of the foot at approximately the base of the $5^{th}$ metatarsal head. This measurement is illustrated in FIGS. 4A-4B for two feet. In one embodiment, the width w is measured below the ball of the foot, and is taken as the width of the foot from medial to lateral edges just below the metatarsal heads. In the drawings, the line denoted as 50 corresponds to the medial edge of the foot at approximately the base of the $1^{st}$ metatarsal head. The line denoted as 52 corresponds to the lateral edge of the foot at approximately the base of the $5^{th}$ metatarsal head. The distance between lines 50, 52 is width w.

Figure 5:
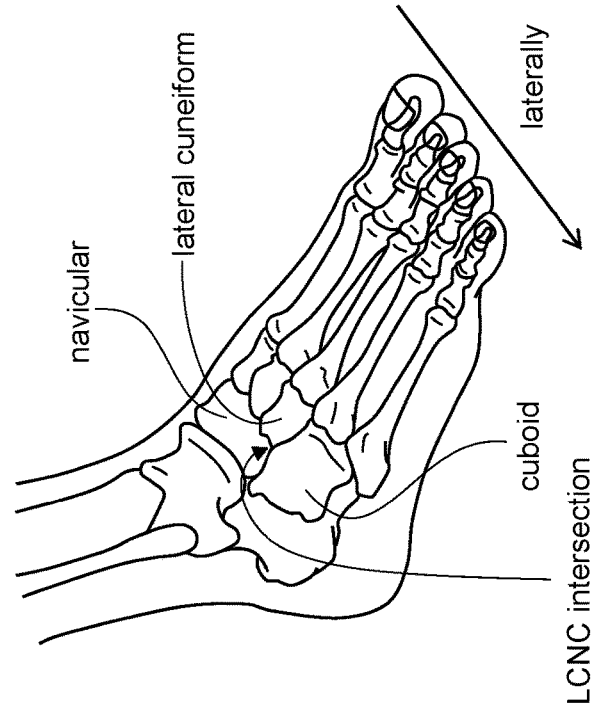
FIG. 5 is an illustration of foot skeleton from a lateral perspective view, showing the bones associated with the "LCNC" complex—the lateral cuneiform, navicular and cuboid bones.

The method also comprises optionally measuring a height h of the lateral arch of a foot in the area at or just lateral to the intersection of the lateral cuneiform, navicular and cuboid bones. FIG. 5 is an illustration of a foot skeleton from a lateral perspective view. The bones in the LCNC complex—the lateral cuneiform, navicular and cuboid bones— are noted, as is their intersection. The arrow along the toes of the foot indicates the lateral direction. From this drawing the position for measuring a height h of the lateral arch of a foot in the area at or just lateral to the intersection of the LCNC complex can be visualized.

In one embodiment, the height h is measured with the foot in an adjusted or restored position. An adjusted or restored position is understood by first considering an "initial bone state" of a foot, which refers to the relationships of the bones in a patient's foot in a first, unrestored configuration/relationship before adjustment or manipulation of the bones, such as by treatment with an orthotic designed in accord with the present methods and systems. An unrestored configuration intends a foot that has one or more foot structures (joints, bones, etc.) in a configuration that is not anatomically or physiologically aligned—also referred to in the art as 'collapsed'. A "restored bone state" or "adjusted bone state" refers to the configuration/relationship of the foot bones that is different from an initial (unrestored) bone state, and in a preferred embodiment refers to the configuration/relationship of foot bones that is a physiologically or medically desired position. These terms are further described and illustrated in U.S. Pat. Nos. 7,926,363; 8,075,501; 8,109,014 and 8,596,145, which are incorporated by reference herein. A foot can be placed in an adjusted bone state by manual manipulation of one or more bones or by manipulation of one or more bones using an instrument, such as a pin bed array. In one embodiment, an adjusted bone state is achieved by manipulating one or more bones in the midfoot region of the foot. "Midfoot" refers to five of the seven tarsal bones (the navicular, cuboid, and the three cuneiforms). The distal row of the midfoot contains the three cuneiforms and the cuboid. The proximal row of the midfoot consists of the cuboid and the navicular. The three cuneiforms articulate proximally with the navicular bone.

Figure 6A:
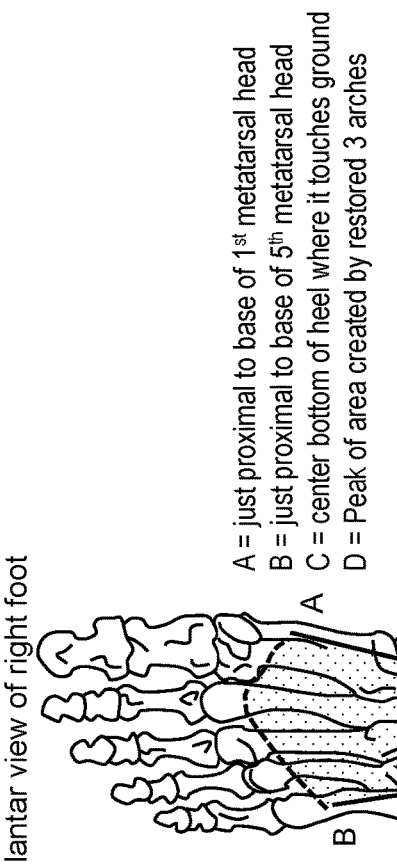
FIGS. 6A-6B are plantar and medial views, respectively, of a foot showing the foot arches and the plantar vacuity or plantar vault relative to ground (or a plane)
Figure 6B:
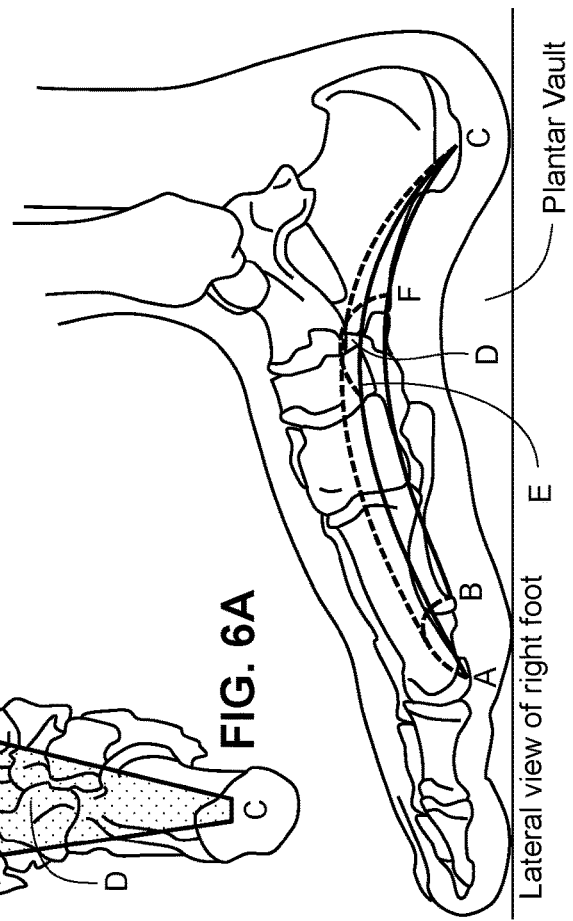
Figure 6C:
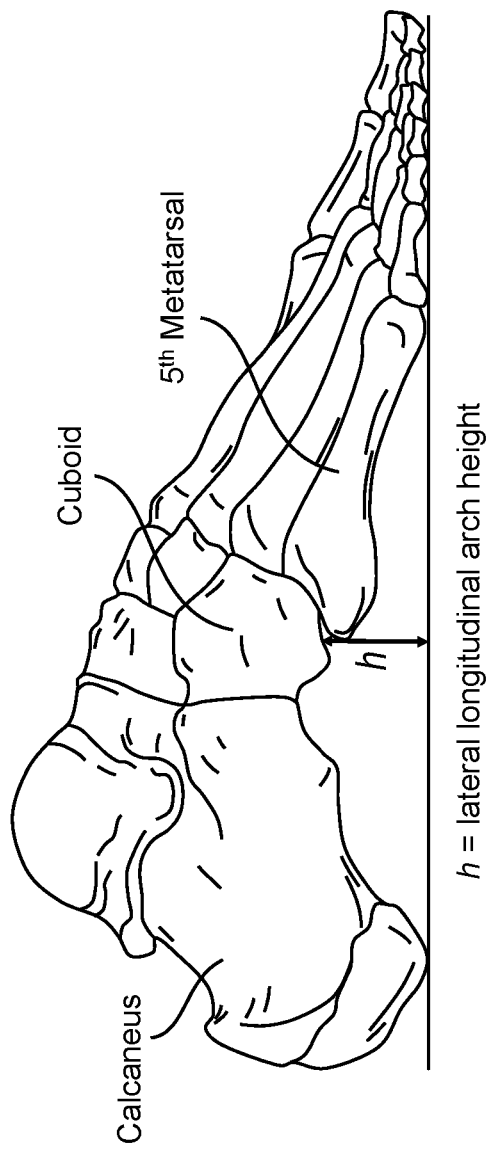
FIG. 6C is a lateral view of a foot showing the lateral foot arch and the plantar vacuity or plantar vault relative to ground (or a plane)

A volume v corresponding to a vacuity defined by the height of the medial, lateral and/or transverse foot arches relative to ground correlates with measured height h, as now to be described. With reference to FIGS. 2A-2D and to FIGS. 6A-6C, the vacuity or "plantar vault" or "plantar dome" that is defined by the region under the three arches of the plantar surface of the foot and the ground is shown. Reference herein to 'ground' intends any planar surface on which a foot is or can be placed. With reference to FIG. 6B, the medial arch is denoted by the line A-C. The lateral arch is denoted by the line B-C, and the transverse arch is denoted by the lines A-B and E-F. The volume of the vacuity varies according to the height of the foot arches and the length of the arches, as well as the width of the foot. Most simply, the vacuity is defined by the plantar topography of the foot and ground (denoted by the solid line under the foot in FIG. 6B). The volume of the vacuity can be measured when the person is seated, standing or partially standing, and mathematically corresponds to the volume under the parabolic arch created by the three foot arches (area=½$r^2$(θ−sin θ). In one embodiment, volume v is approximated as the length of A-C times the foot width (e.g., distance between A and B in FIG. 6B times lateral arch height h (FIG. 6C). In another embodiment, the volume of the vacuity is measured when the person is seated, standing or partially standing with a foot on an instrument that scans the plantar surface of the foot with one or more bones in a restored or adjusted state, and the area under a curve corresponding to the arches and shape of the vacuity is calculated. In another embodiment, lateral arch height h is measured, and is correlated with volume v based on a database from a population of foot measurements of volume and lateral arch heights.

In another embodiment, height h is correlated to volume of a vacuity determined or calculated using a medial arch height, where volume of a vacuity is determined using a measured height h (i.e., lateral arch height h) value that is less than a measured medial arch height by a numerical factor, and/or a (calculated) medial arch height that is calculated to be a value greater than the measured lateral arch height h by a fixed numerical factor. These concepts are discussed further below and herein.

A volume v of the vacuity can be determined in a variety of methods. For example, volume v of the vacuity can be, in one embodiment, determined from a statistical average of measurements of the vacuity of feet in a population of feet after manipulation of each foot (manually or with an instrument) to position one or more bones in the midfoot to a restored state and measuring the dimensions of the vacuity to determine an average or median volume v of vacuity in a population of feet. Alternatively, the volume v can be selected from at least two volumes $v_1$ and $v_2$ (which can be assigned an identifier, such as "low" or "medium"), where the at least two volumes $v_1$ and $v_2$ are determined from vacuity measurements obtained from a population of feet manipulated into an adjusted or restored state. In another embodiment, the volume v is selected from 2, 3, 4 or 5 volumes each assigned an identifier, such as $v_1$, $v_2$, $v_3$, $v_4$, and $v_5$, or F, L, M, MH, H, where the at least two identified volumes were determined from vacuity measurements of a population of feet manipulated into an adjusted or restored state.

In any of these embodiments, the volume v for each foot in the population can be calculated or determined using a height value for the medial arch that is determined as follows. In one embodiment, the medial arch height value used to determine volume v is calculated by increasing the measured lateral arch height h (measured with the foot in restored or adjusted state (i.e., manually manipulated or manipulated with an instrument at the LCNC region)) by a numerical factor. Stated differently, the volume v is calculated or determined using a medial arch height value that is greater than the measured lateral arch height h (where lateral arch height h is measured with the foot in its restored position by instrument or manual manipulation of the LCNC region) by a numerical factor. In another embodiment, the medial arch height value used to determine volume v is determined by measuring the height of the medial arch when the foot is in its restored or adjusted state (i.e., manually manipulated or manipulated with an instrument at the LCNC region), and then reducing the measured medial arch height by a numerical factor. Stated differently, the volume v is calculated or determined using a medial arch height value that is less than a measured medial arch height relative to ground while sitting or standing or partially standing with the foot in its restored position by instrument or manual manipulation of the LCNC region. Reference to 'ground' intends any plane of reference, not necessarily ground as in the earth or a floor.

In yet another embodiment, the measured medial arch height is reduced to an adjusted medial arch height such that the adjusted medial arch height is greater than the measured lateral arch height h by the numerical factor.

In any of the embodiments disclosed herein that reference a numerical factor, the numerical factor is a value between about 0.38 cm to about 0.89 cm (0.15-0.35 inches), or between about 0.46 cm to about 0.81 cm (0.18-0.32 inches), or between about 0.51 cm to about 0.76 cm (0.20-0.30 inches), or between about 0.45 cm and about 0.55 cm (about 0.18-0.22 inches), or between about 0.45 cm to about 0.64 cm (0.18-0.25 inches), or between about 0.40 to about 0.60 cm (about 0.16-0.24 inches), or between about 0.42 to about 0.58 cm (about 0.16-0.23 inches), or between about 0.47 cm to about 0.52 cm (about 0.18-0.20 inches). The numerical factor can also be any discrete value in these ranges, for example, 0.37 cm, 0.38 cm, 0.39 cm, 0.40 cm, 0.41 cm, 0.42 cm, 0.48 cm, 0.49 cm, 0.50 cm, 0.51 cm, 0.52 cm, 0.53 cm, 0.54 cm, 0.55 cm, 0.56 cm, 0.57 cm, 0.58 cm, 0.59 cm, 0.60 cm, 0.61 cm, 0.62 cm, 0.63 cm, 0.64 cm, 0.65 cm, 0.66 cm, 0.67 cm, 0.68 cm, 0.69 cm, 0.70 cm, 0.71 cm, 0.72 cm, 0.73 cm, 0.74 cm, 0.75 cm, 0.76 cm, 0.77 cm, 0.78 cm, 0.79 cm, 0.80 cm, 0.81 cm, 0.82 cm, 0.83 cm, 0.84 cm, 0.85 cm, 0.86 cm, 0.87 cm, 0.88 cm, 0.89 cm, 0.90 cm.

Collectively, length $l_1$, and/or, width w, and/or height h (the height h in some embodiments being correlated via a database to a volume v) provide guidance for selection of an orthotic device that is sized appropriately for an individual foot. In some embodiments, reference to orthotic 'size' intends an orthotic length and width. In other embodiments, reference to orthotic 'size' intends an orthotic length. In other embodiments, reference to orthotic 'size' intends an orthotic length, where the length is provided at different widths and/or different arch heights.

In one embodiment, one or all of the measurements length $l_1$, width w and height h is/are collected on a foot covered with a sock. In another embodiment, one or all of the measurements length $l_1$, width w and height h are collected on a naked foot. In another embodiment, the length $l_1$ is determined, the width w is determined and/or the height h is determined and/or the volume v is determined based on an image of a foot. The image may be an x-ray image, a pressure map image, a photograph, a video, a map constructed using a laser beam applied to the foot, or from an image taken from a cast or crush box impression of the foot, or the like.

In some feet, such as if there is a bony projection from the calcaneus bone, length $l_1$ is taken from a most proximal point of the base of the heel—i.e., from the bony projection.

The method contemplates collecting at least two of the measurements described above in order to recommend or determine size of an orthotic for a foot. The collected measurements permit determination of size of a foot orthotic, and in some embodiments, in addition permit recommending an alternative size of an orthotic product.

Various methods and systems for taking the measurements for use in the method are contemplated, and several are now to be described for purposes of illustration. In a first embodiment, a pin bed system, such as that described in U.S. Pat. Nos. 7,926,363; 8,075,501; 8,109,014 and 8,596,145 and in U.S. Patent Publication No. 2014/0360033, each of which is incorporated by reference herein, is used to obtain an image of a foot. The image is used to determine the length $l_1$, width w, height h. From these measurements the optimal or correct size of orthotic device for a foot (which may be two different sizes for a single individual due to differences in individual feet) is determined and, optionally, one or two alternative sizes are suggested.

In another embodiment, a pin-bed device is used to measure the length $l_1$, width w, and/or lateral arch height h. The volume v can also be measured using a pin-bed device. From the measurements, a software program in the device calculates orthotic size and one or more alternative sizes for a person to try. Alternatively, a chart or matrix that correlates the measurements to an orthotic size is used to determine appropriate orthotic size.

In another embodiment, a manual instrument is used to measure length $l_1$, width w, and/or height h. One suitable instrument is the Brannock shoe size device (shown in U.S. Pat. No. 1,725,334, incorporated by reference herein) or similar instrument. The device provides for measuring separately the left foot and the right foot, as does the known Brannock device. A sliding concave structure is positioned on the device such that it is on the medial side of a foot placed on the device. The concavity of the sliding structure is placed on the medial aspect of the foot at approximately the $1^{st}$ metatarsal head. The opposing side of the concavity has a pointer and scale that corresponds to length $l_1$ (distance from the base of the heel to the base of the first metatarsal head). The instrument also comprises a side-to-side sliding structure to measure the width w at a point just behind the metatarsal heads. In one embodiment, width w is not measured at the foot's widest point, which is typically at the ball of the foot. The width can be read as an absolute measurement (inches or mm), and this measurement alone or in conjunction with the interior width of the footwear to be used determines the width w to be used in the method herein. The instrument may also include a guide or ruler that is perpendicular to the surface on which the instrument is placed in order to measure lateral arch height h when the user manually adjusts the midfoot region of the foot using, for example, a belt or strap.

Figure 8B:
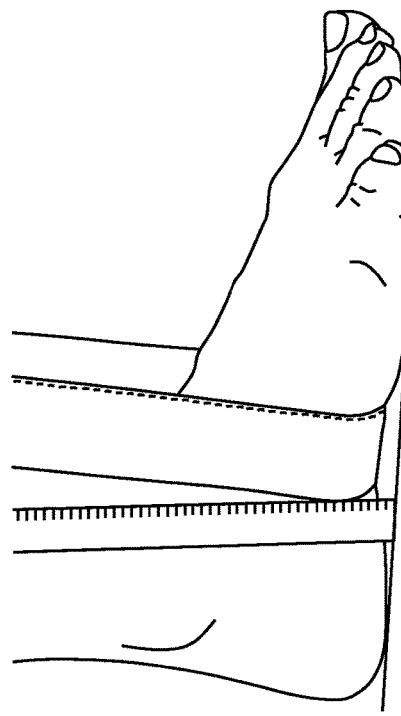
FIGS. 8A-8C illustrate a technique for an individual to manually manipulate his/her midfoot region using for example a belt or strap, to restore the foot structures and then measure lateral arch height h with the foot in a restored condition (or state)
Figure 8C:
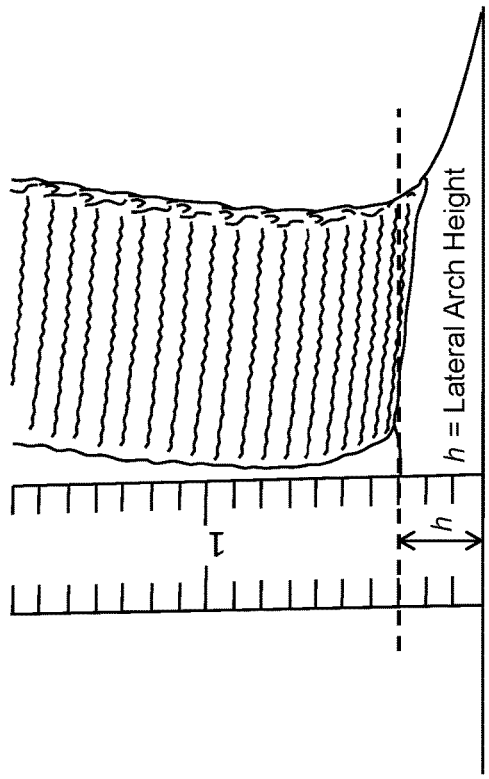
Figure 8A:
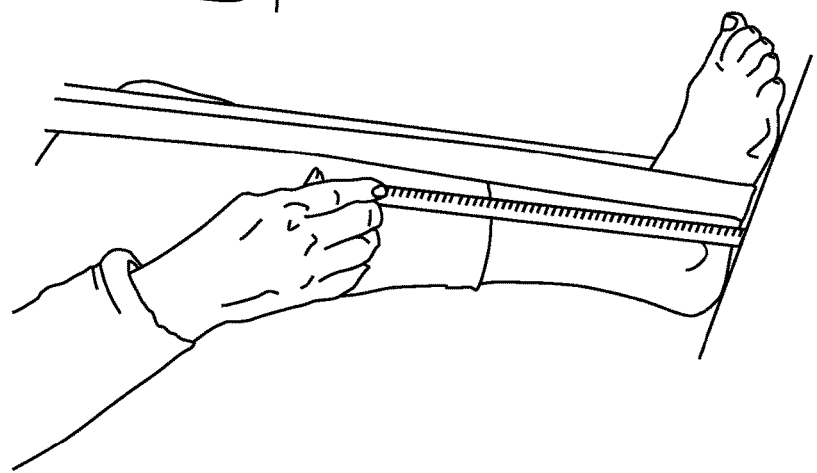
Figures 9A, 9B:
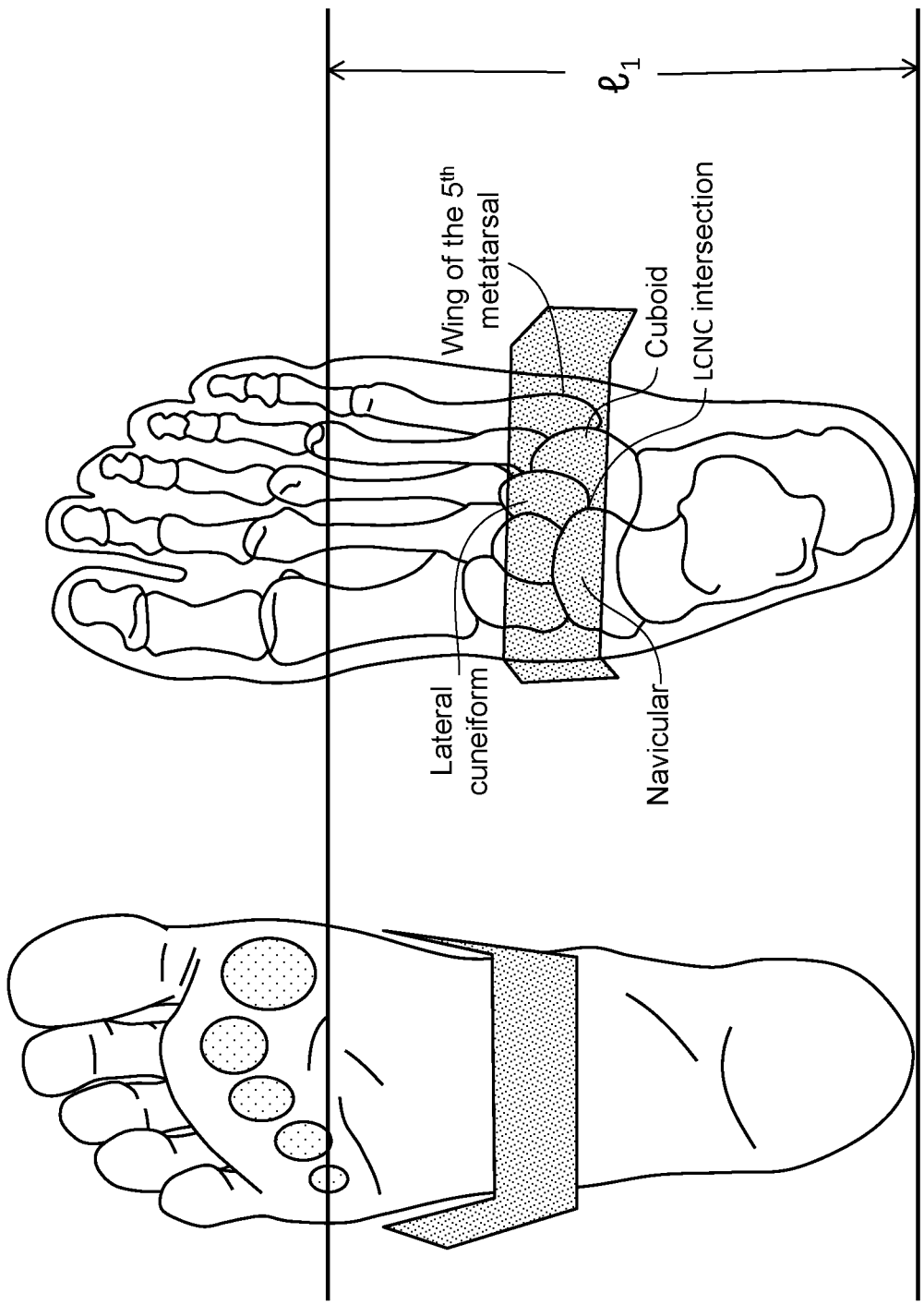
FIGS. 9A-9B are illustrations of a plantar surface of a right foot (FIG. 9A) and a top of a right foot (FIG. 9B) to indicate placement of a device (such as a belt or strap) to manually adjust the midfoot region to a restored state for measurement of lateral arch height h.

Manual adjustment of the midfoot region to measure length $l_1$ and height h in a foot can also be achieved as illustrated in FIGS. 8-10. As shown in FIG. 8A, the person in a seated position places his/her foot on a flat surface, in this case the floor. A manipulation device, such as a belt, cord, strap, fabric length, etc., is passed under the foot at about the mid-section so that the manipulation device contacts the wing of the $5^{th}$ metatarsal on the lateral side of the foot and divides in approximate half the longitudinal medial arch on the medial side of the foot, as seen best in FIGS. 9A-9B. The person then exerts enough pressure on the manipulation device to move at least one bone in the midfoot which will restore the foot's arches. The calcaneus will also tilt in the sagittal and/or frontal planes, further restoring proper anatomic arch heights. The pressure on the manipulation device is desirably sufficient to result in restoration of the foot's arches with the heel and the ball of the foot remaining in contact with the flat surface. Height h of the foot's lateral arch is then measured, as illustrated in FIGS. 8B-8C.

Figure 10A:
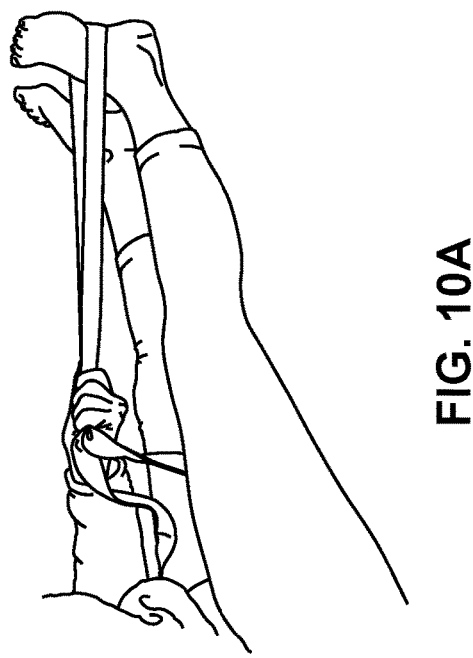
FIGS. 10A-10C illustrate a technique for a seated individual to manually manipulate his/her midfoot region to measure length $l_1$ with the foot in its restored condition.
Figure 10B:
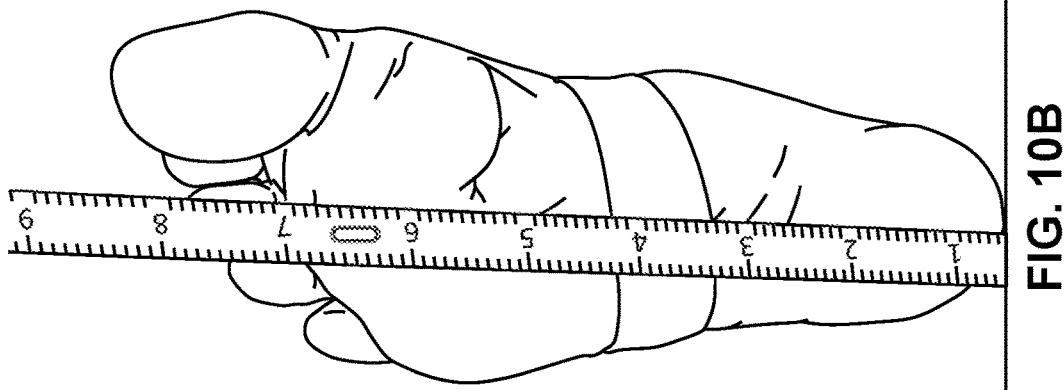
Figure 10C:
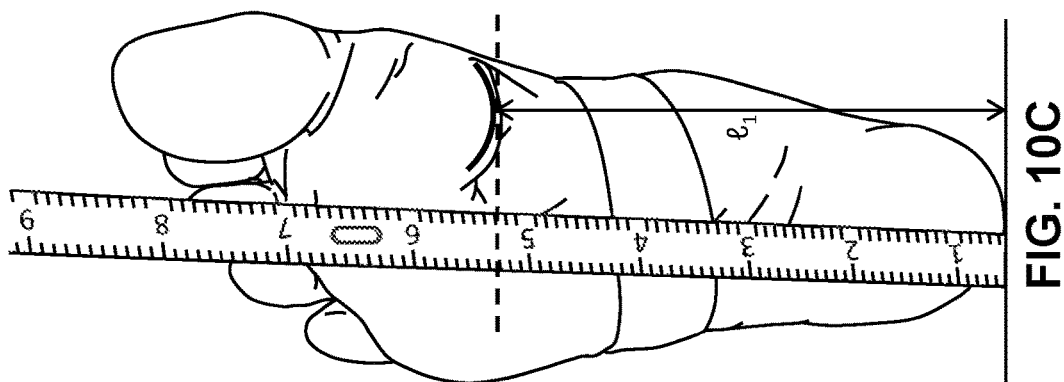

Next, to measure foot length $l_1$, the individual sits on a flat surface with both legs extended, as illustrated in FIG. 10A. The manipulation device is passed about the foot plantar surface at a position as described above with reference to FIG. 8A—across the mid-section of the foot so it covers the wing of the $5^{th}$ metatarsal on the lateral side of the foot and approximately divides the medial arch in half on the medial side of the foot (FIGS. 9A-9B). The manipulation device has a length sufficient to extend from the individual's hands and about the foot. A tension is applied to the manipulation device by the individual, to move at least one bone in the midfoot which will restore height to the arches in the foot. The calcaneus will also tilt in the sagittal and/or frontal planes, further restoring proper anatomic arch heights. The pressure on the manipulation device is desirably sufficient to result in the foot length (from heel to toe) becoming perpendicular to the flat surface on which the individual sits. The back of the heel preferably remains on the flat surface. A measurement is then taken from the flat surface (which is equivalent to the most proximal aspect of the bottom of the person's heel) to the base (most proximal portion) of the foot's first metatarsal head, length $l_1$, as illustrated in FIGS. 10B-10C. In many feet, the proximal edge of the $1^{st}$ metatarsal head can be determined by a crease located at the proximal portion of the ball of a person's foot at the level of the big toe as shown in FIGS. 10B-10C. Alternatively, the head of the $1^{st}$ metatarsal is found and a measurement just below its proximal edge is taken.

Length $l_1$ may also be determined, in other embodiments, by taking a picture of the medial side of the foot when the person is seated and the manipulation device is in place about the foot and pressure applied to adjust a midfoot bone, whilst keeping the heel and ball of the foot on the floor. Length $l_1$ is then determined from the picture by measuring from the most proximal portion of the heel to the most proximal portion of the ball of the foot behind the big toe.

It will be appreciated that once an individual desirous of an orthotic device obtains measurements for length $l_1$ and height h, the measurements along with necessary personal information can be provided on-line or via an app to order a custom orthotic device. In one embodiment, a selection of 3-5 orthotics with a Functional Foot Size that conforms to the customer's measurements are shipped to the individual, from which the individual can select one or more to keep and return the others. It will also be appreciated that the manual manipulation technical can be conducted in a retail store or clinic rather than by an individual.

In some embodiments, to determine the height h or volume v using a manual instrument, a domed or convex insert is secured on the instrument in the position of the foot vacuity when the foot is placed on the manual instrument or is adjusted at the midfoot region with a manipulation device as described above. Inserts of at least three sizes that correspond approximately to low arch, medium arch and high arch foot types are provided to be secured on the instrument. A user tries one, two, three or more of the inserts to identify the one that is most comfortable and best makes contact with the plantar surface of his/her foot in the plantar dome in a restored foot shape without being overcorrected. The insert size corresponds to height h or volume v. As discussed above, in some embodiments height h is correlated to volume of a vacuity having a medial arch height, where the height h is less than the medial arch height by a numerical factor. The numerical factor can be a value in any of the ranges set forth above. In one embodiment, the measured medial arch height is reduced to an adjusted medial arch height such that the adjusted medial arch height is greater than the measured lateral arch height h by the numerical factor.

Accordingly, in another aspect, a system to determine size of an orthotic is contemplated. The system comprises a means to measure dimensions of a foot when placed on, in or in contact with the system or a component of the system, and instructions to measure one or more of or at least two of the following:

(i) a length $l_1$ corresponding to a distance from a proximal heel point to a base of the first or the fifth metatarsal head;

(ii) a width w corresponding to a distance from the medial edge of the foot at approximately the base of the first metatarsal head to the lateral edge of the foot at approximately the base of the fifth metatarsal head; and (iii) a height h corresponding to the height of the lateral foot arch relative to ground.

The system also comprises a size selection matrix that correlates length $l_1$, width w and/or height h to an orthotic size.

In all of the embodiments and aspects described herein, it is contemplated that the orthotic be of the type to be inserted into footwear or be footwear itself (e.g., a shoe, sandal, etc. having a built-in footbed that is an orthotic footbed).

Figures 7A, 7B:
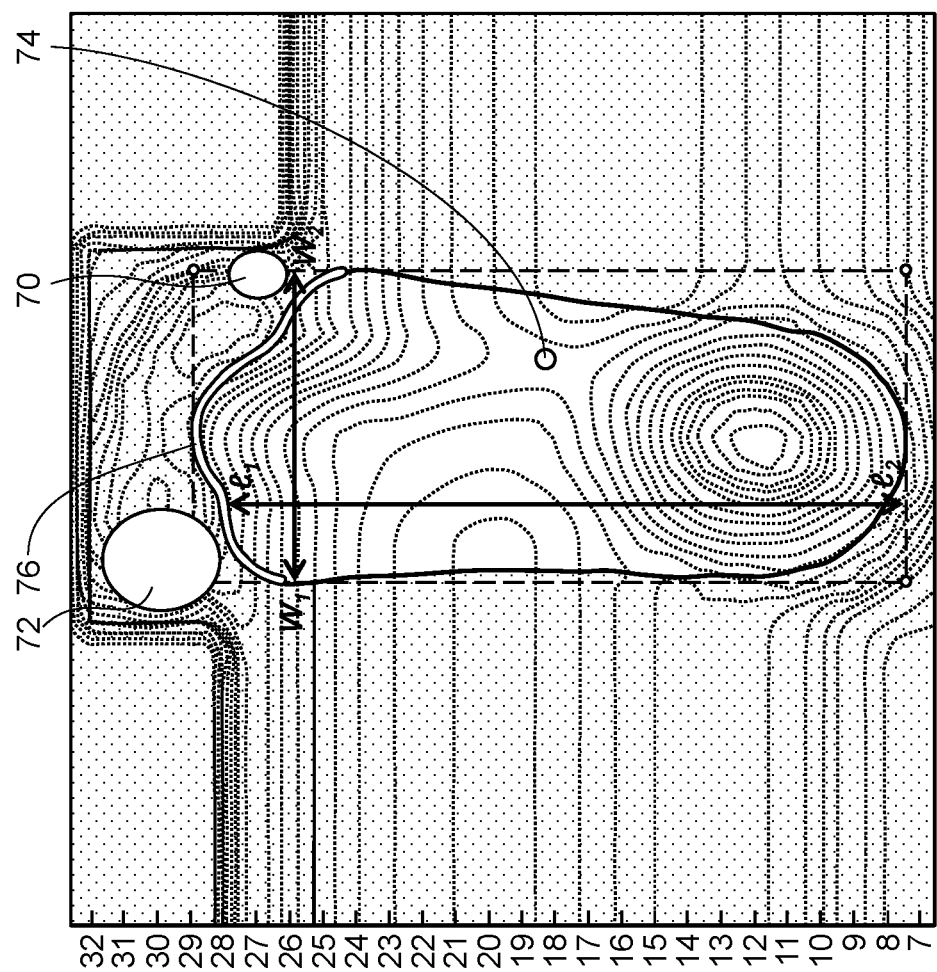
FIGS. 7A-7B are a digital image of a right foot taken with an instrument designed and configured to determine a functional foot volume based on measurements of foot width, length from heel to first metatarsal head or fifth metatarsal head, and height of lateral arch, where

In one embodiment, the means to measure foot dimensions is an automated instrument that provides an image or map of the foot being measured. An exemplary image is depicted in FIGS. 7A-7B, where the position of the $1^{st}$ and $5^{th}$ metatarsal heads, indicated respectively as 70, 72, are indicated for use as positional markers to determine the length $l_1$ and width w (FIG. 7A). Length $l_1$ is indicated in FIG. 7A as the line extending from $l_1$ to $l_2$, and width w is indicated in FIG. 7A as the line spanning from $w_1$ to $w_2$. The peak of the lateral arch is also determined from the image and is denoted at 74 in FIG. 7A. FIG. 7A also illustrates what is meant by the term undulating distal trim line, by the solid double line indicated at 76. In another embodiment, the means is a device operable manually, such as the modified Brannock device described above.

The system, in another embodiment, comprises instructions to measure a length $l_1$ corresponding to a distance from a proximal heel point to a base of the first or the fifth metatarsal head; and a size selection matrix that correlates length $l_1$ to a foot orthotic size.

An alternative system to determine size of a foot orthotic comprises instructions to measure at least two of (i) a length $l_1$ corresponding to a distance from a proximal heel point to a base of the first or the fifth metatarsal head; (ii) a width w corresponding to a distance from the medial edge of the foot at approximately the base of the first metatarsal head to the lateral edge of the foot at approximately the base of the fifth metatarsal head; and (iii) a height h corresponding to the height of the lateral foot arch relative to ground; and a size selection matrix that correlates the two measurements to an orthotic size.

In one embodiment, the system further comprises a device to measure length $l_1$ and width w. In another embodiment, the system further comprises a device to determine height h.

In another aspect, a library of foot orthotics is provided. The library comprises a collection of foot orthotics, each orthotic in the collection assigned a size that corresponds to a measurement of length $l_1$ taken as a distance from a proximal heel point to a base of the first or the fifth metatarsal head. Each orthotic size in the collection is provided in one width w or in at least two different widths w. By way of example, the table below summarizes such a library where orthotics having a size identified numerically as size 1, size 2, size 3, size 4, size 5, size 6 and size 7 is provided, where the orthotic size corresponds to a fixed range of length $l_1$ in inches (although other dimensions such as centimeters or millimeters is contemplated). As a point of comparison and to illustrate how the method of sizing described herein (and referred to as Functional Foot Size (FFS)) differs from what is known in the art as 'shoe size', the shoe size for men and for women in U.S. sizes is shown in the right hand side of the table.

Orthotic Size as Measured versus Shoe Size

| Functional Foot Size (Orthotic Size) | | Corresponding U.S. Shoe Size | |
| --- | --- | --- | --- |
| Size | $l_1$ in inches | Men | Women |
| 1 | 5.25 to <6.0 | 7.5-9.5 | 5.5-9.0 |
| 2 | 5.75 to <6.25 | 8.0-9.0 | 6.5-10.0 |
| 3 | 6.0 to <6.5 | 7.5-11.0 | 6.5-10.0 |
| 4 | 6.25 to <6.75 | 8.0-11.0 | 7.0-11.5 |
| 5 | 6.5 to <7.0 | 8.0-13.0 | 8.5-12.0 |
| 6 | 6.75 to <7.25 | 8.0-14.0 | 9.0-12.0 |
| 7 | 7.0 to <7.5 | 9.0-16.5 | |

In one embodiment, the library comprises a collection of orthotics assigned a size ranging from 1 to n, where n is 2, 3, 4, 5, 6, 7, 8, 9, 10, 11, 12, 13, 14, 15, 20, 25 or more. Each orthotic size in the library is provided in at least one width. In other embodiments, each orthotic size in the library is provided in at two widths or three widths or four widths or five widths or more. For example, in one embodiment, the library comprises orthotics with sizes 1, 2, 3, 4, 5, 6, and 7, each orthotic available in three widths designated as, for example, narrow, medium, and wide. In another embodiment, each orthotic size in the library is provided in at least one volume and in other embodiments each orthotic size in the library is provided in two volumes, three volumes, four volumes or more, where volume corresponds to the foot vacuity. It will be appreciated that each orthotic in the library can be provided at each size and at each width and at each volume, providing a range of size (length), width, and volume combinations. In one embodiment, each orthotic in the library at each size is provided in 2 volumes, low and medium, that are chosen based on measured height h. In another embodiment, each orthotic in the library at each size is provided in 3 volumes, low, medium and high, that are chosen based on measured height h.

Accordingly, in one embodiment, each size of orthotic in the collection is provided in at least two different heights h corresponding to the height of the lateral foot arch relative to ground. In another embodiment, each size of orthotic in the collection is provided in at least two different volumes corresponding to a vacuity defined by medial, lateral and transverse foot arches relative to ground and selected based on a user's measurement of height h of lateral foot arch relative to ground. In another embodiment, height h is correlated to volume of a vacuity having a medial arch height, where the height h is less than the medial arch height by a numerical factor, and ranges of the factor are provided above. In one embodiment, the volume v is selected from at least two volumes v assigned an identifier, such as "low" or "medium", where the at least two volumes v are determined from vacuity measurements of a population of feet manipulated into an adjusted or restored state. In one embodiment, the volume v is selected from 2, 3, 4 or 5 volumes assigned an identifier, such as F, L, M, MH, H, where the at least two identified volumes were determined from vacuity measurements of a population of feet manipulated into an adjusted or restored state. The volume v can, in any of these embodiments, have a height dimension that is greater than the measured lateral arch height h by a numerical factor and/or that is less than a measured medial arch height relative to ground while sitting or standing or partially standing. In one embodiment, the measured medial arch height is reduced to an adjusted medial arch height such that the adjusted medial arch height is greater than the measured lateral arch height h by the numerical factor.

FIGS. 11A-11B are illustrations of a foot from different individuals. The foot in FIG. 11B has an overall foot length —as measured from the base of the heel to the distal end of the longest toe —that is greater (longer) than the foot in FIG. 11A. The orthotic device selected to be the correct size for these two feet according to the method and system described herein is the same, as represented by the shaded area in the drawing. The measurements of length $l_1$ (corresponding to a distance from a proximal heel point to a base of the first or the fifth metatarsal head) and of width w (corresponding to a distance from the medial edge of the foot at approximately the base of the first metatarsal head to the lateral edge of the foot at approximately the base of the fifth metatarsal head) are approximately the same for the feet in FIGS. 11A-11B, even though the foot in FIG.11B is a shoe size larger than the foot in FIG. 11A. The term FFS in FIGS. 11A-11B is an abbreviation for functional foot size, which in this example, encompasses the measurements length $l_1$ and width w.

FIGS. 12A-12B illustrate two feet having the same shoe size yet requiring a different orthotic size when measured according to the system and method described herein. The foot in FIG. 12A has a longer (greater) length $l_1$ (corresponding to a distance from a proximal heel point to a base of the first metatarsal head) than the foot in FIG. 12B. The orthotic device selected to be the correct size for these two feet according to the method and system described herein are not the same, even though the shoe size based on overall length of the foot (from heel to distal tip of longest toe) is the same. The term FFS in FIGS. 12A-12B is an abbreviation for functional foot size, which encompasses the measurements length $l_1$ and width w.

Figure 13C:
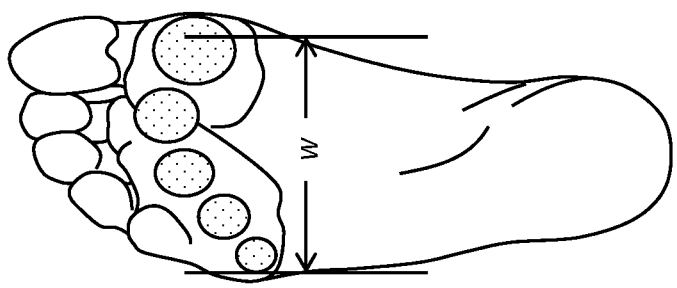
FIGS. 13A-13C are illustrations of the plantar surface of a foot, where
Figure 13B:
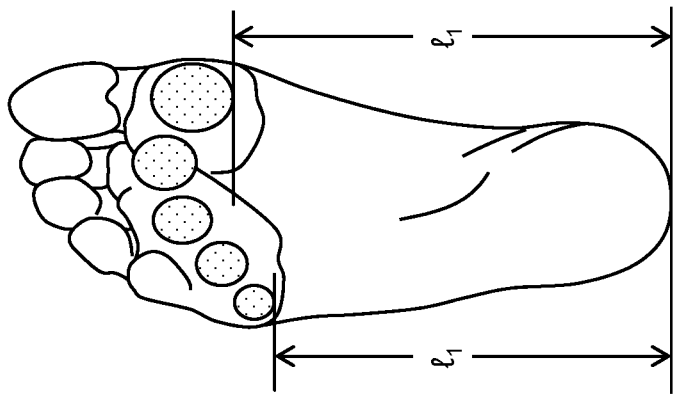
Figure 13A:
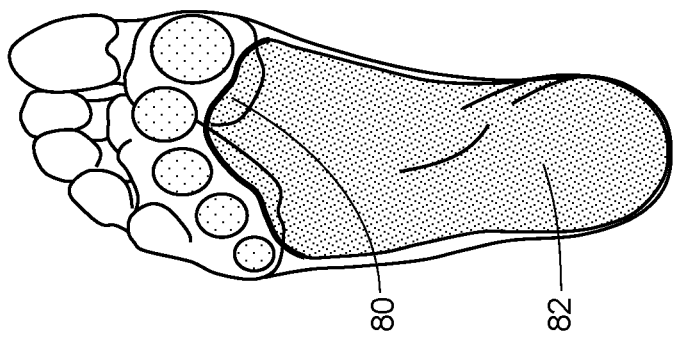

It can also be seen from FIGS. 11A-11B and FIGS. 12A-12B that the orthotic device provided in the library herein has a unique distal trim line (abbreviated as DTL is some drawings). The distal trim line is shown in FIG. 13A by identifier 80. Orthotic device 82 is sized by the method described herein to have a length $l_1$ (corresponding to a distance from a proximal heel point to a base of the first metatarsal head; FIG. 13B). Width of orthotic 82 is determined by measuring width w corresponding to a distance from the medial edge of the foot at approximately the base of the first metatarsal head to the lateral edge of the foot at approximately the base of the fifth metatarsal head (FIG. 13C). The trim line of the orthotic device at the distal end undulates to fit at the base of the metatarsal heads for all five metatarsals and is a bell-shaped curve rather than a straight or simple curved line across the foot width, as best seen in FIG. 13A. Accordingly, in one embodiment, each orthotic in the collection has an undulating distal trim line.

In other embodiments, each orthotic in the collection of foot orthotics is manufactured from, for example, a carbon fiber composite material, a plastic or thermoplastic material, a polymeric material, a polymeric blend, a cork material, and the like. In another embodiment, each orthotic is intended to be inserted into footwear. In another embodiment, each orthotic in the collection is a piece of footwear.

In another aspect, a library of shoe orthotic devices is provided, where the library comprises a plurality of orthotics with sizes that correspond to the range of possible orthotic sizes selected from the method described herein.

From the foregoing, certain aspects and features of the claimed method can be appreciated. The joints and other foot structures function optimally when aligned anatomically to a physiologically optimal configuration. The method herein is based in part on a finding of certain anatomical configurations that exist when foot structures are physiologically aligned, and that a foot should be placed in its physiologically aligned configuration when evaluation and measuring that foot to design a custom orthotic. For example, in a properly aligned foot, a first line drawn from the center of the heel up the lateral column to the head of the $5^{th}$ metatarsal and a second line drawn from the head of the $5^{th}$ metatarsal to the head of the $1^{st}$ metatarsal will have an angle between about 95-105°. Further, regardless of 'shoe size' as understood in its traditional sense of foot length from heel to tip of longest toe, the restored height of the lateral arch will be approximately 0.50 cm (about 0.2 inches) for a low volume foot (where volume is created by the three arches together forming a dome or vault under the functional area of the foot—heel to head of the metatarsals), about 0.75 cm (about 0.3 inches) for a medium volume foot, and about 1.0 cm (about 0.4 inches) for a high volume foot.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for selecting size of a foot orthotic, comprising:
    determining a length $l_1$ corresponding to a distance from a back of a heel to approximately a base of a metatarsal head of a foot;
    determining a height h of a lateral arch of the foot, the height h corresponding to a distance between a surface on which the foot is placed to a plantar surface of the foot approximately at an intersection defined by a lateral cuneiform bone, a navicular bone and a cuboid bone; and
    selecting a foot orthotic size based on length $l_1$ and height h,
    wherein determining a length $l_1$, determining a height h or both is performed on a foot manipulated to adjust one or more bones of the foot to a restored position.

2. The method of claim 1, wherein the length $l_1$ is taken as the distance from the back of the heel to the base of the first metatarsal head.

3. The method of claim 1, wherein the length $l_1$ is taken as the distance from the back of the heel to the base to the base of the fifth metatarsal head.

4. The method of claim 1, wherein the length $l_1$ is taken from a most proximal point of the base of the heel.

5. The method of claim 1, wherein determining a height h comprises determining the height h corresponding to a distance between a surface on which the foot is placed to a plantar surface of the foot in an area lateral to the intersection of the lateral cuneiform, navicular and cuboid bones.

6. The method of claim 1, wherein said determining is performed on a foot that is manually manipulated to adjust one or more bones of the foot to a restored position.

7. The method of claim 1, wherein said determining is performed on a foot that is manipulated using a device or instrument to adjust one or more bones of the foot to a restored position.

8. The method of claim 1, wherein the one or more bones comprise one or more bones in the midfoot.

9. The method of claim 8, wherein the bones in the midfoot comprise bones in the lateral cuneiform-navicular-cuboid (LCNC) complex.

10. The method of claim 1, further comprising determining a width w corresponding to a distance from a medial edge of the foot at approximately the base of the first metatarsal head to a lateral edge of the foot at approximately the base of the fifth metatarsal head.

11. The method of claim 10, wherein selecting a foot orthotic size comprises selecting a foot orthotic size based on length $l_1$ and height h and a foot orthotic width based on width w.

12. The method of claim 10, wherein selecting a foot orthotic size comprises selecting a foot orthotic size based on length $l_1$ and a foot orthotic width based on width w.

13. The method of claim 1, wherein selecting further comprises selecting a foot orthotic size from a library of sizes for foot orthotics.

14. The method of claim 13, wherein the library comprises a library of orthotic sizes based on length $l_1$ and height h, wherein each size is available in the library at more than one width.

* * * * *